(12) United States Patent
Bagwan et al.

(10) Patent No.: US 10,828,016 B2
(45) Date of Patent: Nov. 10, 2020

(54) FLUID DELIVERY DEVICE

(71) Applicant: SECRETARY, DEPARTMENT OF BIOTECHNOLOGY, New Delhi (IN)

(72) Inventors: Siraj Bagwan, Bangalore (IN); Jonathan Pillai, Pune (IN); Hanish Sharma, Chattisgarh (IN); Pramod Garg, New Delhi (IN); Govind Makharia, New Delhi (IN)

(73) Assignee: Secretary, Department of Biotechnology, New Delhi (IN)

( * ) Notice: Subject to any disclaimer, the term of this patent is extended or adjusted under 35 U.S.C. 154(b) by 0 days.

(21) Appl. No.: 14/913,107

(22) PCT Filed: Dec. 16, 2013

(86) PCT No.: PCT/IN2013/000772
§ 371 (c)(1),
(2) Date: Feb. 19, 2016

(87) PCT Pub. No.: WO2015/025328
PCT Pub. Date: Feb. 26, 2015

(65) Prior Publication Data
US 2016/0199045 A1 Jul. 14, 2016

(30) Foreign Application Priority Data
Aug. 21, 2013 (IN) ............ 2471/DEL/2013

(51) Int. Cl.
*A61B 10/02* (2006.01)
*A61M 5/32* (2006.01)
*A61B 17/00* (2006.01)

(52) U.S. Cl.
CPC ...... *A61B 10/0233* (2013.01); *A61B 17/0057* (2013.01); *A61B 17/00491* (2013.01);
(Continued)

(58) Field of Classification Search
CPC .......... A61B 10/0233; A61B 17/00491; A61B 17/0057; A61B 2017/00495;
(Continued)

(56) References Cited

U.S. PATENT DOCUMENTS 4,915,695 A * 4/1990 Koobs ................... A61M 5/315
222/137
5,380,286 A * 1/1995 van den Haak ... A61M 5/31511
604/110
(Continued)

FOREIGN PATENT DOCUMENTS

| WO | WO 99/34734 | 7/1999 |
| WO | WO 01/67961 | 9/2001 |
| WO | WO 02/051300 | 7/2002 |

OTHER PUBLICATIONS

International Search Report for PCT/IN2013/000772 dated Apr. 28, 2014, 4 pages.

*Primary Examiner* — Kevin C Sirmons
*Assistant Examiner* — Tezita Z Watts
(74) *Attorney, Agent, or Firm* — Seed IP Law Group LLP

(57) ABSTRACT

According to an embodiment, the present subject matter describes a device for delivery of one or more fluids in to a target site. The fluid delivery device (100) includes a housing (105, 205), a shaft (110), which may 125 be disposed inside the housing (105, 205) to form at least one fluid chamber (115, 210) therebetween. Further, the fluid chamber (115, 210) is adapted to receive the one or more fluids. The fluid delivery device (100) further includes a plunger (120, 225) provided at a first end (125) of the housing (105, 205). The plunger (120, 225) may be coupled to the shaft (110) and may be adapted to move inside the housing (105, 205) to deliver the one or more fluids to the target site (405).

11 Claims, 6 Drawing Sheets

(52) U.S. Cl.
CPC ... *A61M 5/3295* (2013.01); *A61B 2017/0065* (2013.01); *A61B 2017/00495* (2013.01); *A61B 2017/00632* (2013.01); *A61B 2017/00654* (2013.01); *A61B 2217/007* (2013.01)

(58) Field of Classification Search
CPC .. A61B 2017/00632; A61B 2017/0065; A61B 2017/00654; A61B 2217/007; A61M 5/3295; A61M 37/00; A61M 37/0015; A61M 5/3148; A61M 5/31578; A61M 2005/323
See application file for complete search history.

(56) References Cited

U.S. PATENT DOCUMENTS

| | | | | |
|---|---|---|---|---|
| 5,788,673 A | * | 8/1998 | Young | A61M 5/14526 604/131 |
| 5,814,022 A | * | 9/1998 | Antanavich | A61B 17/00491 604/181 |
| 5,833,654 A | * | 11/1998 | Powers | A61M 39/0208 604/93.01 |
| 5,868,711 A | * | 2/1999 | Kramer | A61B 17/3472 604/136 |
| 6,702,760 B2 | * | 3/2004 | Krause | A61B 10/0233 600/564 |
| 7,169,114 B2 | * | 1/2007 | Krause | A61B 10/0266 600/435 |
| 7,785,298 B2 | * | 8/2010 | Schwab | A61M 37/0069 604/218 |
| 2003/0097079 A1 | * | 5/2003 | Garcia | A61B 10/0275 600/567 |
| 2007/0106176 A1 | | 5/2007 | Mark et al. | |
| 2008/0121657 A1 | | 5/2008 | Voegele et al. | |
| 2009/0024056 A1 | * | 1/2009 | Bacon | A61B 10/0233 600/567 |
| 2010/0121284 A1 | * | 5/2010 | Hexsel | A61M 5/329 604/264 |
| 2013/0026255 A1 | * | 1/2013 | Hamman | A61B 3/005 239/461 |
| 2013/0060203 A1 | * | 3/2013 | Svensson | A61M 5/31596 604/222 |
| 2014/0324022 A1 | * | 10/2014 | Scribben | A61M 5/20 604/506 |

\* cited by examiner

FLUID DELIVERY DEVICE

This application is the U.S. national phase of International Application No. PCT/IN2013/000772 filed 16 Dec. 2013 which designated the U.S. and claims priority to IN Patent Application No. 2471/DEL/2013 filed 21 Aug. 2013, the entire contents of each of which are hereby incorporated by reference.

TECHNICAL FIELD

The present subject matter relates, in general, to medical devices and, in particular, to a fluid delivery device for multiple medical procedures.

BACKGROUND

Various medical procedures are implemented for various purposes, for example, certain medical procedures involve extraction of tissue samples from a target site and delivery of fluids at the target site. One example of such a medical procedure is biopsy. Biopsy involves extraction of tissue samples from body tissues to diagnose various health conditions, such as liver diseases, peptic ulcers, kidney diseases, and to identify malignant or benign tumors in the body tissues. Generally, biopsy of internal organs carries a risk of perforating internal blood vessels during operation, thereby causing some amount of internal haemorrhaging. Usually the volume of tissue extracted during the biopsy is typically small and the probability of perforating a major vessel to cause uncontrolled hemorrhaging resulting in significant morbidity or mortality is also very small; but in certain cases it may lead to uncontrolled internal hemorrhaging. However, the benefit of obtaining an accurate diagnosis from biopsied tissue generally outweighs the risk of post-biopsy internal hemorrhaging. This is especially true for biopsies done under visual or radiographic guidance.

Additionally, for unguided medical procedures in highly vascularized organs, such as spleen, kidneys, brain, and lungs, the risk of internal hemorrhaging is high enough to discourage wide-spread adoption of such medical procedures, despite their high diagnostic value. For example, percutaneous biopsy procedures of the liver and kidneys may cause internal hemorrhage, which can quickly lead to fatal results if left uncontrolled.

SUMMARY

This summary is provided to introduce concepts related to devices for delivering fluids to a target site. These concepts are further described below in the detailed description. This summary is not intended to identify essential features of the claimed subject matter nor is it intended for use in determining or limiting the scope of the claimed subject matter.

According to an embodiment, the present subject matter relates to a fluid delivery device for delivering one or more fluids to a target site. The fluid delivery device comprises a housing and a shaft disposed inside the housing to form at least one fluid chamber therebetween for receiving the one or more fluids. The fluid delivery device further includes a plunger coupled to a first end of the housing. Additionally, the plunger may be coupled to the shaft and the plunger may be adapted to move inside the housing to deliver the one or more fluids from the fluid chamber to the target site.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1A:
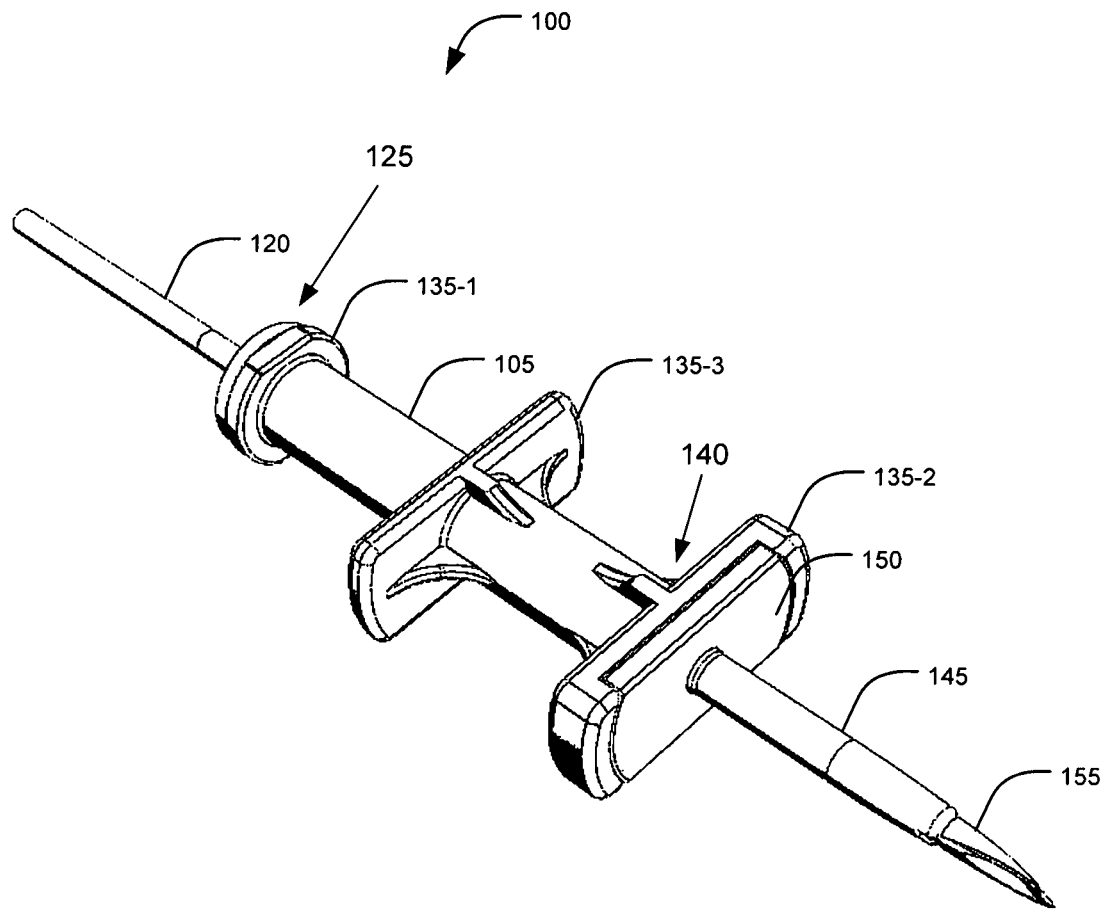
FIG. 1a and FIG. 1b illustrate a device for delivering fluids, in accordance with an embodiment of the present subject matter.

The present subject matter relates to a fluid delivery device used for medical procedures, such as needle biopsy and laparoscopy. The device is used to provide one or more fluids to a target site, such as a body tissue, which is to be examined. Additionally, in parallel to delivery of the fluids, the fluid delivery device may be used to extract tissue samples for further medical procedures.

During medical procedures, such as biopsy, there is a general risk of internal hemorrhage, which may be fatal in certain cases. Generally, in order to prevent hemorrhage, a separate procedure of providing a hemostatic agent, at the target site, after the biopsy may be performed. To arrest the internal hemorrhage a minimum of a two-step protocol is to be followed. In other words, a first procedure is performed to extract a tissue sample and thereafter a second procedure is perform to provide the hemostatic fluid. Further, for a percutaneous needle biopsy procedure, a patient may have to remain perfectly still and simultaneously hold his breath for the entire duration of the initial needle biopsy procedure as well as the subsequent delivery of the hemostatic agent. The patient is generally required to hold the breath for a span of 10-20 seconds, depending on the biopsy procedure followed, to avoid motion-induced laceration and aggravated hemorrhaging of internal organs following the insertion of a biopsy needle and devices for delivery of the haemostatic agent. However, it may not be possible for patient for example, patients with compromised respiration, children, elderly, critically-ill patients, and sedated patients, to hold the breath for a longer duration. Further, there may be cases where the patient is subjected to multiple samplings if the tissue sample is inadequate, or due to variability in sample quality, thereby not only causing discomfort to the patient but also increasing the chances of internal hemorrhage.

Furthermore, existing devices for delivery of the hemostatic agents often fail to maintain positive pressure at the target site, thereby allowing drainage and loss of the hemostatic agent from a tissue cavity. This in turn may result in inadequate or inconsistent hemostasis, thereby reducing the efficacy of the medical procedure.

According to an embodiment of the present subject matter, a device to facilitate concurrent delivery of one or more fluids while performing a medical procedure is described herein. Such a device may be used for a variety of medical applications, for example, biopsy, laparoscopy, and delivery of fluids having multiple components, where these components are to be mixed at the target site. The device includes a plunger provided at a first end of a housing and at least one cannula provided at a second end of the housing. A shaft is disposed in the housing such that at least one fluid chamber is formed between an inner surface of the housing and the outer surface of the shaft. The fluid chamber is adapted to receive one or more fluids. In an example, where multiple fluids are to be delivered, multiple compartments may be formed between the inner surface of the housing and the outer surface of the shaft. Further, each compartment may function as a fluid chamber and receive one type of fluid. Further, in an implementation, the plunger, the shaft, and the cannula may be coupled such that they are in tandem or adjacent to each other. Further, in example, the plunger, the shaft, and the cannula may be coupled such that they are co-axial.

In an implementation, the plunger, the shaft, and the cannula may be coupled such that a motion of the plunger inside the housing is translated into a corresponding motion of the cannula. In an example, a forward motion of the plunger inside the housing, translates into forward motion of the shaft and simultaneously, pressure on the fluids enclosed in the fluid chambers is built, thereby pushing the fluids to the cannula. The cannula may deliver the fluid to the target site. Thus, in case where the medical procedure involves collection of a sample from a target site, the fluid may be delivered to the target site prior to tissue collection, while collecting the sample, or after collecting the sample. Further, since the shaft and the cannula remain inside the target site, such as a tissue, for the entire duration of the fluid delivery, a positive pressure is built up inside the tissue cavity. After the shaft is retracted, the tissue may collapse around the opening of the tissue cavity and the positive pressure may be maintained. Thus, as soon as the tissue is cut, the hemostatic agent is immediately delivered into a capillary bed of the tissue. As a result, instead of blood oozing out from the vascular organ, the hemostatic agent enters capillaries and thus aids hemostasis in local environment.

Further, the volume of fluid delivered may be in excess of the volume of the sample retracted during the procedure. As a result, even if fluid loss occurs after fluid delivery, an adequate amount of the fluid may still be retained inside the tissue cavity due to the positive pressure. Thus, in case of biopsy, since the positive pressure is maintained, a requisite amount of the hemostatic agent may be delivered, thereby aiding in hemostatic action.

Additionally, since the forward motion of the plunger in the housing, not only provides for collection of sample but also provides for concurrent delivery of fluids to the target site during a medical procedure like biopsy, a separate process for delivering the fluids, such as hemostatic agents, may not be required. Thus, the patients may hold the breath for shorter durations, thereby reducing the discomfort caused to the patients during such medical procedures and also minimizing the chances of internal injuries. Further, the concurrent hemostasis along with the medical procedure minimizes the chances of internal hemorrhage, thereby encouraging the use of percutaneous procedures.

These and other advantages of the present subject matter would be described in greater detail in conjunction with the following figures. While aspects of described systems for fluid delivery devices can be implemented in any number of different systems, environments, and/or configurations, the embodiments are described in the context of the following exemplary system(s).

Figure 1B:
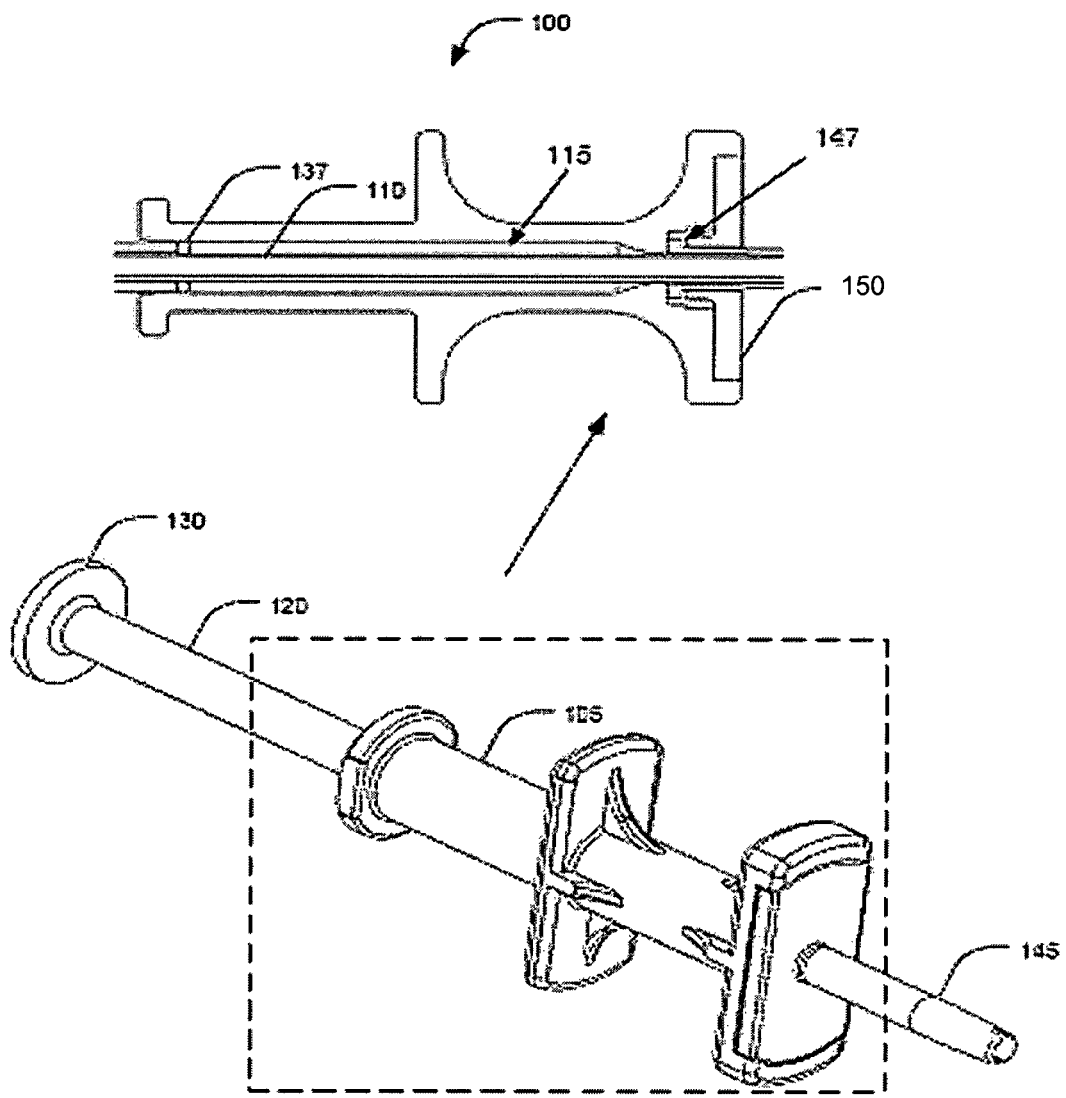

FIG. 1a and FIG. 1b illustrate a fluid delivery device 100 for delivering one or more fluids to a target site, according to an embodiment of the present subject matter. Although the present subject matter has been explaied in considerable detail with respect to biopsy procedure; however it will be understood that the fluid delivery device 100, may be used for other applications as well. For example, the fluid delivery device 100 may be used in laparoscopy. For the sake of brevity, the description with reference to FIG. 1a and FIG. 1b is provided in conjunction.

According to an embodiment, the fluid delivery device 100, hereinafter referred to as device 100, includes, for example, a housing 105 having a central lumen to accommodate a shaft 110 and one or more fluids (not shown in figures). The shaft 110 may have a diameter narrower than the central lumen and may be disposed inside the central lumen to form a fluid chamber 115 between an inner surface of the housing 105 and an outer surface of the shaft 110. Further, the shaft 110 may be disposed inside the cavity to form a fluid cavity, which functions as a fluid chamber 115. In an example, the shaft 110 and the housing 105 may be cylindrical in shape and the shaft 110 may be disposed inside the housing 105 to form a circumferential cavity, which functions as the fluid chamber 115. The fluid chamber 115 is adapted to receive the fluids to be delivered to a target site, such as a liver tissue. In said embodiment, the fluid chamber 115 may include a single fluid; however in other embodiments, the device 100 may include multiple fluid chambers to receive two or more fluids as will be explained in detail with reference to description of FIG. 2a and FIG. 2b. Examples of fluids include, but are not limited to, hemostatic agents; isotonic saline; alcohols; polyethylene glycol, such as CoSea™ and AdvaSeal-S™; Cyano-acrylate glue, such as Dermabond®; thrombin; fibrin glue, such as Tisseel™, Hemaseel™, Beriplast P™, Bolheal™, and Quixil™; a combination of a collagen and a cross-linker, such as gelatin matrices and gluteraldehyde; a combination of thrombin and gelatin; and a combination of Bovine Serum Albumin and cross-linker gluteraldehyde.

Further, the device 100 may include a plunger 120 adapted to move inside the housing 105. The plunger 120 may be provided from a first end 125 of the housing 105 and may be integrally connected to the shaft 110. The plunger 120 may also include a plunger flange 130, which abuts against a first locator flange 135-1 provided on the first end 125 of the housing 105, as illustrated in FIG. 1a. Furthermore, the plunger 120 may be coupled to the housing 105 such that it is co-axial with the shaft 110. Also, the plunger 120 may be adapted to move inside the housing 105 and an outer diameter of the plunger 120 and an internal diameter of the housing 105 may be substantially same. Since the plunger 120 may be integrally connected to the shaft 110, translation of the plunger 120 results in a corresponding translation of the shaft 110.

The plunger 120 may include a first sealing unit 137, such as an O-ring, provided at a housing-plunger end, i.e., the end of the plunger 120 that connects to the housing 105. The first sealing unit 137 provides a hermetic seal between the inner surface of the housing 105 and the outer surface of the shaft 110. Thus, the first sealing unit 137 provides a leak proof encapsulation of the fluid in the fluid chamber 115. In an implementation, the housing 105 may have a variable cross-section along the length of housing 105. For instance, the housing 105 may have a circular cross-section and varying diameter. For instance, the cross-section may become narrower from the first end 125 to a second end 140. Thus, when the plunger 120 is moved forward in the housing 105, the first sealing unit 137 fits tightly inside the constricting cross-section, thereby providing efficient sealing and preventing backflow of the hemostatic agent. However, in other implementations, the housing 105 may have a constant cross-section.

According to an embodiment, at the second end 140 of the housing 105, at least one cannula 145 may be provided, the cannula 145 being adapted to be inserted inside the target site. Further, the cross-section bf the cannula 145 may constrict from an end coupled to the housing 105, i.e., the housing-cannula end to a fluid delivery end, i.e., the end from where the fluid may be delivered to the target site. Furthermore, at a cannula-housing end, i.e., an end of the cannula 145 that connects to the housing 105, the cannula 145 may have a cross section substantially narrower than the second end 140 of the housing 105. The varying cross section provides for coupling of the cannula 145 with the housing 105 and at the same time facilitates entry of the cannula 145 in the target site. In an example, the cannula 145 may be made of a softer material than that of the housing 105. The cannula 145 may be made of a material, such as Low Density Polyethylene (LDPE) thick film or silicone, in order to prevent injury to a tissue. However, it will be understood that the cannula 145 may also be made of a harder material or metals, such as stainless steel.

In one implementation, the cannula 145 may be fastened to the second end 140 to ensure that the cannula 145 remains integral with the housing 105 throughout the medical procedure. The cannula 145 may be fastened using the fastening element 150. In an example, the fastening element 150 may be a component that is press-fit into a second locator flange 135-2 and the component takes the shape of the recess therein. In other examples, the fastening element 150 may be a screw and nut arrangement, rivet(s), or snap-fit part(s). The fastening element 150 may also be fastened by a permanent or temporary adhesive. Alternately, a permanent fastening method, such as ultrasound welding, may used to fasten the fastening element, for example, in case where the entire assembly is disposable. Further, in case the cannula 145 is made of metal, the cannula may be welded.

The fastening element 150 may fit into the second locator flange 135-2 provided on the housing 105. The second locator flange 135-2 abuts against skin of a patient and provide for easily locating the cannula 145 with respect to the skin of the patient, during the medical procedure. The housing 105 may also include a third locator flange 135-3. The first, second, and third locator flanges 135-1, 135-2, and 135-3 may be collectively referred to as flanges 135. Further, the flanges 135 may be provided to secure the device 100 to a corresponding medical unit, such as a biopsy device. Additionally, the corresponding medical device may be manually operated or may be automated.

Figure 3A:
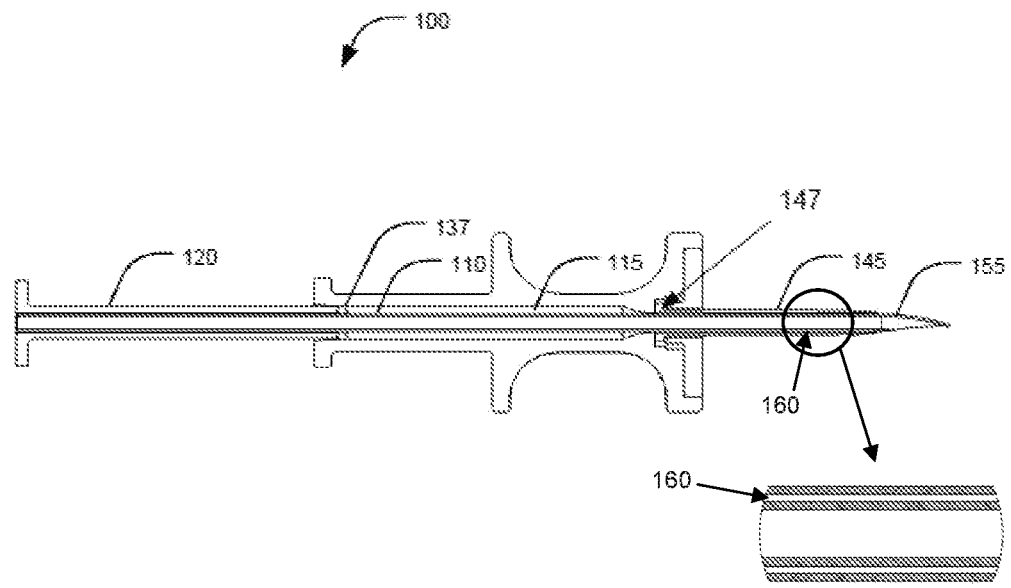
FIG. 3a and FIG. 3b illustrate cross-section views of the device in an un-deployed state and a deployed state, respectively, in accordance with an embodiment of the present subject matter.
Figure 3B:
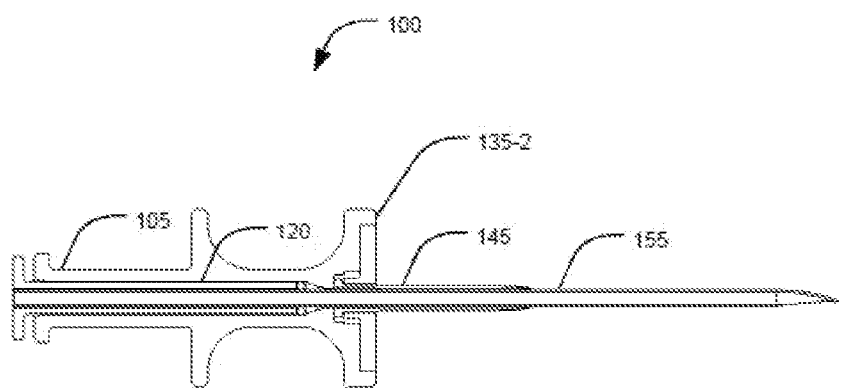

Referring back to the cannula 145, in an implementation, to the cannula 145, the plunger 120, and the housing 105 may be coaxial with each other, as illustrated in FIG. 3a and FIG. 3b. Further, at a housing-cannula end, i.e., an end of the cannula 145 that connects to the housing 105, the cannula 145 may have diameter substantially similar to the second end 140 of the housing 105. In an example, the diameter of the cannula 145 may constrict from the housing-cannula end to a fluid delivery end, i.e., the end from where the fluid may be delivered to the target site. The varying diameter provides for coupling of the cannula 145 with the housing 105 and at the same time facilitates, entry of the cannula 145 in the target site. Also, the cannula 145 may be coupled to the housing 105 to form a cavity 147 between an outer surface of the cannula 145 and the inner surface of the housing 105.

The cavity 147 may receive the fluid from the fluid chamber 115 when shaft 110 is moved forward inside the housing 105 to deliver the fluid to the target site.

In an implementation, to have the fluid delivered to the target site, the device 100 may further include a translation mechanism to translate a forward motion of the plunger 120 into the forward motion of the cannula 145. In an example, the translation mechanism may include a coupling between the cannula 145 and the shaft 110. In another example, the translation mechanism may be an independent mechanism of translation that coordinates forward motion of the cannula 145 with that of the plunger 120. For instance, an independent translation mechanism may be a co-axial hollow tube encompassing the housing 105 and acting as a secondary plunger attached to the fastening element 150.

In an alternate implementation, the cannula 145 may be static and connected to a fixed or static surface, such as a front surface of a fastening element 150, other than the shaft 1 10. Further, while the cannula 145 may be static, the secondary component 155 may be free to move. In said implementation, the cannula 145 may be long enough to reach a secondary component 155, which collects the sample. Additionally, the length of the cannula 145 may be such that the cannula 145 delivers fluid deep inside tissue, i.e. at the end of secondary component 155 without the need for any translation. In other words, the cannula 145 may extend along the length of the secondary components 155. Further, the length of the cannula 145 may be adjustable as different lengths may be required for reaching various organs. For instance, the length of the cannula 145 may be selected based on an ultrasound measurement of a distance from the skin to the target organ, say, liver capsule. For example, if the distance from the skin to the liver capsule is 25 mm, then the length of the cannula 145 may be set to 25 mm plus 5-7 mm extra, since the cannula 145 has to pierce through the liver capsule to deliver the fluids and to collect the sample. The length may be adjusted prior to insertion by loosening the fastening element 150. The cannula 145 may move in or out of the fluid chamber 1 15 based on the length to be set and fastening element 150 may be refastened accordingly. Thus, the length of the cannula 145 may be adjusted such that the cannula 145 protrudes into the tissue. Alternately, length may be pre-selected based on the organ to be pierced, i.e., the fluid delivery device 100 may be manufactured with organ specific variations.

During the use of the device 100 for the biopsy procedure, the fluid may be delivered to the target site while a sample is being collected or immediately after the sample is collected. In an example, to collect the sample, the cannula 145 may be adapted to receive a secondary component 155, such as a needle. In a case, where the cannula 145 is static, the secondary component 155 may be pushed forward by the plunger 120 via the shaft 110. The secondary component 155 may be used to collect tissue sample, or insert and anchor the device 100 into the tissue for fluid delivery. The secondary component 155 may be coupled to the cannula 145 to form chamber 160 therebetween to deliver the fluid to the target site. While the secondary component 155 pierces into the target site to collect tissue sample, at the same time the fluid may be ejected from the cavity to the target site. Alternately, the fluid may also be ejected prior or after the tissue collection.

Further, in other examples, the cannula 145 may also directly deliver the fluid to the target site, for instance, in case of a natural body cavity, where the tissue may not be required to be pierced as much as in usual cases of biopsy. For instance, the cannula 145 may be such that the secondary component 155 is completely encased in it prior to the forward motion of the plunger 120, i.e., the cannula 145 can shield the secondary component 155 during entry, say, into a natural body cavity where initial piercing is not necessary. Further, the varying cross-section of the cannula 145 may itself provide adequate tissue displacement to allow insertion of the cannula 145 into the tissue without the use of the secondary component 155 at all.

Further, to ensure leak proof connectivity for fluid flow between the fluid chamber 115 and the cannula 145, at least one second sealing unit (not shown in the figures) may be provided. The second sealing unit may be provided between the second end 140 of the housing 105 and the cannula-housing end of the cannula 145. Further, the second sealing unit may be similar to the first sealing unit 137. Owing to the sealing unit, a unidirectional outlet for the fluid is provided, thereby facilitating localized delivery of the fluid close to a cutting edge of the secondary component 155. Thus, the fluid from the device 100 is delivered to the target site during the medical procedure or immediately after the medical procedure.

In an implementation, the device 100 may include a port (not shown in figures) through which a monitor may be connected for internal imaging. For example, in cases where an imaging fluid is delivered to the target site, say, for laparoscopic related applications, in addition to fluid delivery, internal imaging for further analysis may be performed.

Figure 2A:
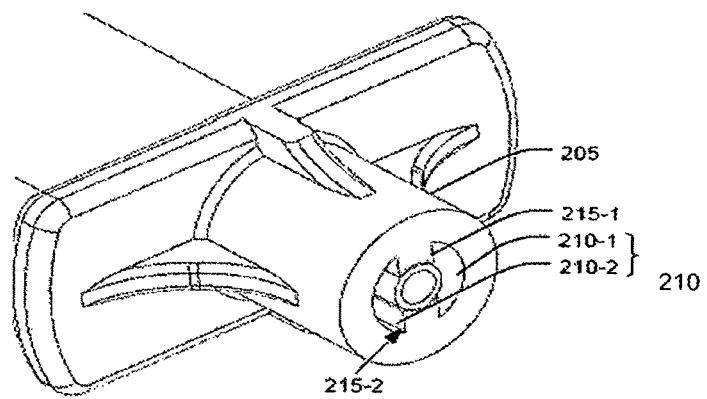
FIG. 2a and FIG. 2b illustrate a magnified view of various components of the device, in accordance with an embodiment of the present subject matter.
Figure 2B:
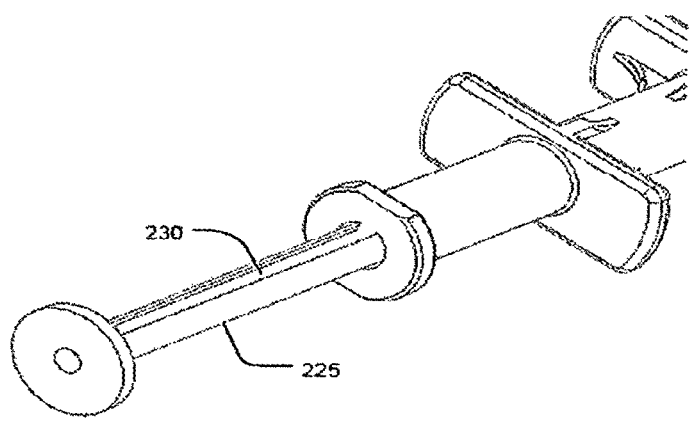

FIG. 2a and FIG. 2b illustrate the device 100, according to another embodiment of the present subject matter. In certain cases, the fluids may have to be provided with an additional component to initiate their pro-coagulation functionality in vivo. For example, the fluids, such as some biological hemostatic agents which may be polymerized or cross-linked, may need an additional component. Further, in such cases, the hemostatic agent, i.e., a first fluid, may have to be kept separate from an initiator, i.e., a second fluid, prior to in vivo delivery to prevent premature activation.

Furthermore, when two independent agents are used, each of which has a different activation profile on contact with blood, each of the agents may require different time windows for activation. For example, the first agent may activate immediately on contact, but may provide temporary stabilization. In contrast, a second agent may require a longer window of time for complete activation, and may persist for a longer duration. Thus, in such cases, the two agents or fluids are to be stored separately in two independent reservoirs while allowing for a mechanism to deliver them to an in vivo location simultaneously, during or immediately following the action of extracting a sample from the target site.

In order to facilitate simultaneous delivery of multiple fluids, according to said embodiment, the device 100 includes a housing 205 divided into two compartments 210-1 and 210-2 by internal splines 215-1 and 215-2, collectively, referred to as the internal splines 215. The internal splines 215 may be provided along a length of the housing. Each of the two compartments 210-1 and 210-2 form a fluid chamber, say, fluid chamber 210 in the present embodiment. Thus, the fluid chamber 115 of previous embodiment is split into two compartments. i.e., the two fluid chambers 210 in the present embodiment. Further, it will be understood that the housing 205 may include multiple internal splines to provide multiple compartments. For example, in case three fluids are to be delivered, the housing 205 may include three internal splines. Alternately, the shaft 110 may have external splines provided along the length of the shaft 110. The external splines may cooperate with the internal splines 215 of the housing 205 to form multiple compartments inside the housing 205. In said case, each external splines may be accommodated in a groov formed between two internal splines 215. It will be understood that the dimensions of the internal splines 215 may vary based on the implementation.

Further, as discussed above, the housing 205 may be adapted to receive a plunger 225 at the first end 125. The body of the plunger 225 includes a plurality of grooves 230 to cooperate with the internal splines 215. The movement of the plunger 225 inside the housing 205 is constrained by the plunger flange 130, sealing the first end 125 and the two fluid chambers 210 of the housing 105. When the plunger 225 is disposed inside the housing 205, the groove 230 acts as longitudinal seal, thereby effectively bifurcating the fluid cavity into two smaller independent fluid chambers 210. Each of the fluid chambers 210 may hold different fluids or a pre-defined combination of the agent and its initiator.

In said embodiment, when the plunger 225 is advanced into the housing 205, the fluid constrained in the two fluid chambers 210 may be expelled through second end of the housing 205 towards the cavity 147 formed between the cannula 145 and the housing 205. The two fluids may mix inside the cavity 147, and a combination of the fluids may be delivered out of the cannula 145, similar to the embodiment discussed with reference to FIG. 1a and FIG. 1b described earlier. The mixing may be sufficient to activate both the fluids to perform the necessary action. In an example a rapid ejection of both fluids may create a turbulent flow at the end of the cannula 145. Further, this flow may have spiral eddies that promote mixing within the tight constraints of the cannula 145 and the tissue cavity.

In another embodiment, one or more cannulas 145 may be provided to facilitate ejection of multiple fluids. In said embodiment, one or more compartments 210 may be connected to an independent cannula 145. For example, one cannula 145 may be concentric or coaxial with other.

In yet another embodiment, the splines 215 may be aligned diametrically opposite to each other to divide the fluid cavity into two equal compartments, or to say two fluid chambers 210. Alternately, to have unequal compartments, the splines 215 may also be aligned at an angle, for example, 45°; or the splines 215 may be vertically aligned but off-set from a central axis. Further, the plunger 225 may also be divided into multiple sub plungers, for instance, the plunger 225 may be bifurcated, to slide independently in each fluid chamber 210. The splines 215 may also be aligned radially inside the fluid chambers 210 and the plunger 225 may be adapted to function as a screw that rotates inside the splines 215 as it pushes the fluids into the cannula 145.

FIG. 3a and FIG. 3b illustrate cross-sectional views of the device 100 in an un-deployed position and a deployed state, according to an embodiment of the present matter. Further, FIG. 4a, FIG. 4b, FIG. 4c, and FIG. 4d illustrate a schematic representation of a needle biopsy procedure using the device 100, in accordance with an embodiment of the present subject matter. In an implementation, the device 100 may be prefilled with the fluid to be delivered, say at the time of manufacturing the device 100. Alternately, the device 100 may receive the fluid at the time of performing the medical procedure. Although, FIG. 3a, FIG. 3b and FIG. 4a-FIG. 4d have been explained in considerable detail with respect to biopsy of a tissue using the device 100 for delivering a hemostatic agent; the functioning of the device 100 for other medical procedures will be apparent to one skilled in the art.

Figure 4A:
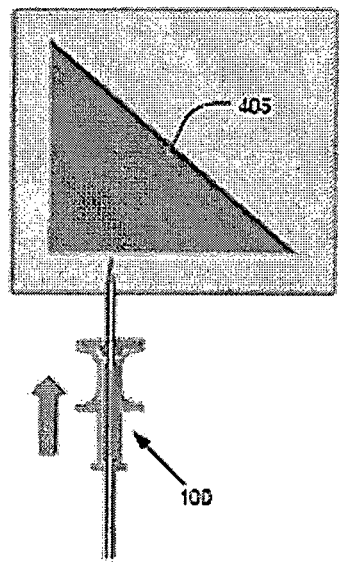
FIG. 4a, FIG. 4b, FIG. 4c, and FIG. 4d illustrate a schematic representation of a needle biopsy procedure using the device, in accordance with an embodiment of the present subject matter.

In order to perform the biopsy, a target site 405, such as a liver capsule, may be identified. Upon identification, the device 100 may be inserted inside the body of the patient such that the device 100 abuts against the skin of the patient using the second locator flange 135-2, as illustrated in FIG. 4a.

Figure 4B:
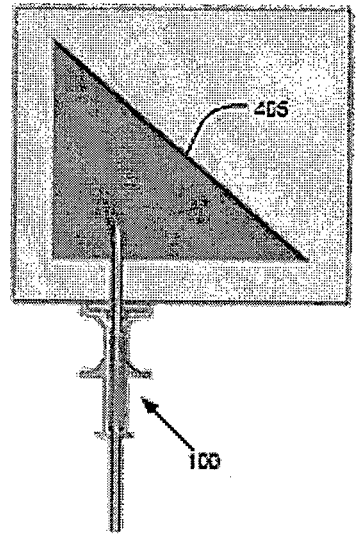

Further, the cannula 145 having the secondary component 155 can be pushed inside the body, by way of the plunger 120, to reach the target site 405 as illustrated in FIG. 4b. Thus, in a deployed state, as illustrated in FIG. 3b, the plunger 120 may be moved closer to the first locator flange 135-1.

Once, the secondary component 155 reaches the target site 405, the plunger 120 may be moved forward and the secondary component 155 is pushed inside the target site 405 to collect tissue sample. Further, in case of a biopsy procedure, the associated medical device may be used to provide aspiration to suck in a sample from the target site. With forward motion and continued aspiration the sample may get accumulated inside the secondary component 155. Further, as soon as the forward motion is complete, the aspiration may be stopped and the plunger 120 may be rotated to give a rotational motion to the secondary component 155 to separate the tissue from organ. Subsequently, while the secondary component 155 is removed from the body of patient, then again aspiration may be provided to suck out the accumulated tissue from the secondary component 155 to transfer it to a sample container.

Figure 4C:
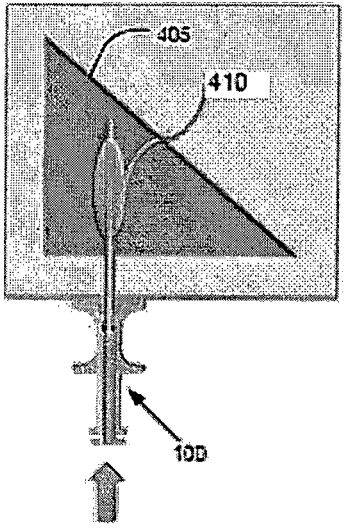

Simultaneously, the forward motion of the plunger 120 inside the housing 105 pushes the shaft 110 to push hemostatic agent 410 inside the fluid chamber 115 to the target site via the cavity 147 as illustrated in FIG. 4c. This results in concurrent delivery of the hemostatic agent 410 to the target site along with the collection of tissue sample. Additionally, since the cannula 145, terminates close to a cutting edge of the secondary component 155, it ensures localized delivery of the hemostatic agent 410 close to the site of potential hemorrhaging.

Further, the length of the stroke of the plunger 120 inside the housing 205 may determine a volume of the hemostatic agent 410 to be delivered at the target site 405. Additionally, a speed at which the plunger 120 translates linearly inside the housing 105 affects the flow rate of fluid delivery. Thus, the plunger 120 provide for controlling the flow and the volume of the hemostatic agent 410 in coordination with the overall dimensions and design of the fluid chamber 115. Therefore, fluid flow may be controlled independent of the action of the shaft 110, i.e., collection of the tissue sample.

Figure 4D:
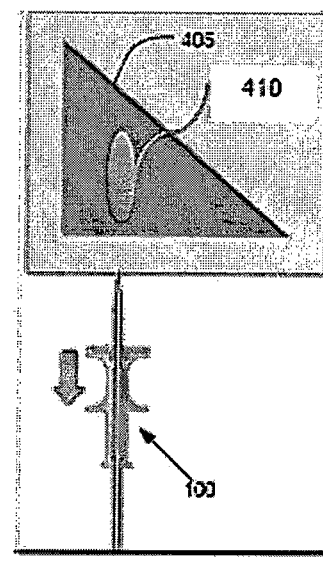

Upon collecting the tissue sample from the target site 405, the shaft 110 may be retracted by way of a backward motion of the plunger 120 as illustrated in FIG. 4d. For example, during the procedure, when it is determined that the secondary component 155 has collected the tissue sample and a requisite volume of the hemostatic agent 410 has been delivered, the secondary component 155 may be retracted.

Since the shaft 110 and the cannula 145 remain inside the target site 405 for the entire duration of the fluid delivery, a positive fluid pressure is built up inside a tissue cavity, which was created due to piercing action of the device 100. After the shaft 110 is retracted, the tissue may collapse around the opening of the tissue cavity, thereby maintaining the positive pressure. Further, to avoid fluid loss, the volume of the hemostatic agent 410 delivered may be in excess of the volume of tissue retracted during the procedure. As a result, even if some fluid loss occurs after delivery, a requisite volume of the fluid may still be retained inside the tissue cavity to maintain the positive pressure to have effective hemostasis.

It will be understood that more than one fluid may be delivered to the target site 405 in the same way as illustrated above. In such cases, the agents from the multiple fluid chambers 210 may be mixed immediately before the fluid delivery in the cavity 147.

Figure 5:
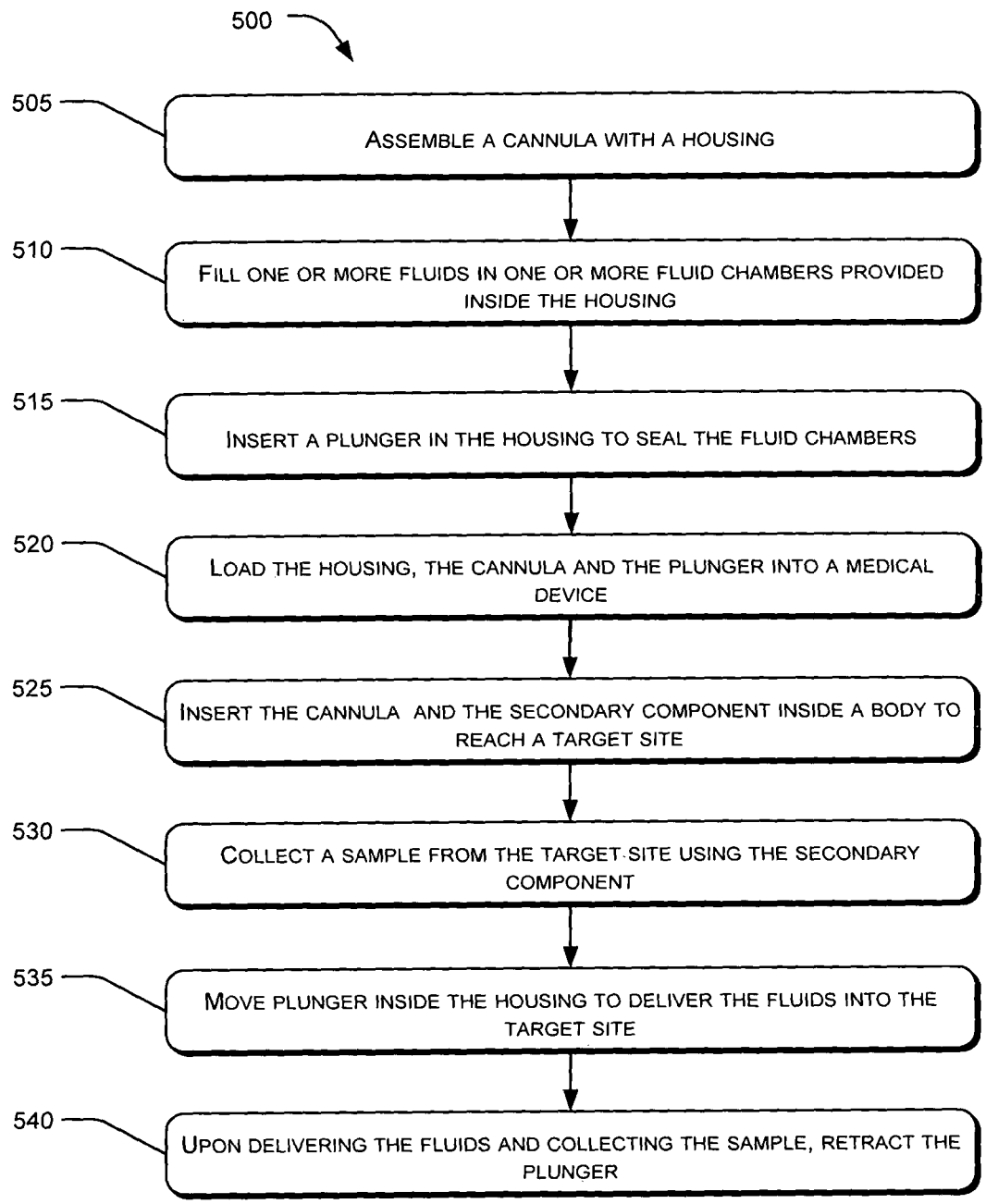
FIG. 5 illustrates a method for delivering one or more fluids to a target site, according to an embodiment of the present subject matter.

FIG. 5 illustrates a method 500 to deliver one or more fluids into a target site, according to an embodiment of the present subject matter. In an implementation, the fluids are delivered using the device 100. The order in which the method 500 is described is not intended to be construed as a limitation, and individual steps may be deleted from the method without departing from the spirit and scope of the subject matter described herein.

At block 505, a cannula, such as the cannula 145 is assembled with a housing. In an example, the cannula may further include a secondary component, such as a needle. Further, the cannula and the secondary component may be sterilized prior to being assembled with the housing. The cannula may be locked with the housing using a fastening element.

At block 510, the one or more fluids are filled in one or more fluid chambers provided inside the housing. In other implementations, the fluid chamber may be prefilled with fluids. For example, a manufacturer may manufacture the device already prefilled with the fluids.

At block 515, a plunger may be inserted in the housing to seal the fluid chambers. The plunger may also include a first sealing unit to provide seal between the fluid chambers and the housing.

At block 520, the housing, the cannula and the plunger may be loaded into a medical device, such as a biopsy device, to perform the corresponding medical action.

At block 525, the cannula and the secondary components may be inserted inside a body to reach a target site.

At block 530, a sample from the target site is collected by the secondary component. For example, a shaft accommodated inside the housing may be rotated or moved linearly to collect the sample.

At block 535, the plunger is moved forward inside the housing to deliver the fluids into the target site.

At block 540, the plunger is retracted, when a requisite volume of the fluids is delivered and the sample is collected. The extraction of the sample creates a cavity in the target site and, as the plunger is retracted, a positive pressure builds up in the cavity. Further, the fluids are retained in the cavity to perform the corresponding action, for example, hemostasis in case of biopsy.

Although embodiments for fluid delivery device for multiple medical applications have been described in language specific to structural features and/or methods, it is understood that the invention is not necessarily limited to the specific features or methods described. Rather, the specific features and methods are disclosed as exemplary embodiments for the fluid delivery device.

We claim:

1. A device configured for delivery of one or more fluids to a target site concurrent to interaction with a tissue sample at the target site, the device comprising:
    a housing having a central lumen;
        a shaft disposed inside the central lumen of the housing to form at least one annular fluid chamber between an inner surface of the housing and an outer surface of the shaft, wherein the at least one annular fluid chamber is configured to receive the one or more fluids;

a secondary component provided at a distal end of the shaft to interact with the tissue sample, wherein the shaft is adapted for coupling with the secondary component;

a cannula provided at a second end of the housing and extending along a length of the secondary component for insertion in the target site along with the secondary component, wherein the cannula receives the one or more fluids from the at least one annular fluid chamber into a chamber formed between the cannula and the secondary component and delivers the one or more fluids to the target site concurrent to the interaction of the secondary component positioned at the target site with the tissue sample; and a plunger provided at a first end of the housing, wherein the plunger is integrally connected to the shaft, and
a forward motion of the plunger inside the housing simultaneously (a) translates into a forward motion of the shaft to insert the secondary component into the target site to interact with the tissue sample, and (b) builds pressure on the one or more fluids in the at least one annular fluid chamber formed between the shaft and the housing to push the one or more fluids into the cannula from the at least one annular fluid chamber to deliver the one or more fluids to the target site concurrent to the interaction with the tissue sample, and wherein the plunger controls the fluid flow through the cannula independent of shaft action.

2. The device as claimed in claim 1, wherein the cannula is fixedly coupled to a static surface; and wherein the secondary component is free to translate in relation to the cannula.

3. The device as claimed in claim 2, wherein the static surface includes a front surface of a fastening element; and wherein the fastening element fastens the cannula to the second end.

4. The device as claimed in claim 1, wherein the cannula is provided at the second end to form a cavity between an outer surface of the cannula and the inner surface of the housing, wherein the cannula receives the one or more fluids flowing from the at least one annular fluid chamber into the chamber formed between the cannula and the secondary component through the cavity.

5. The device as claimed in claim 1, wherein the housing includes a plurality of internal splines provided along a length of the housing to form a plurality of compartments, each compartment functioning as a fluid chamber.

6. The device as claimed in claim 5, wherein the plunger includes a plurality of grooves to cooperate with the plurality of internal splines, wherein the internal splines are provided along the length of the housing.

7. The device as claimed in claim 1, wherein the housing has a variable cross-section along a length.

8. The device as claimed in claim 1, wherein the housing has a plurality of locator flanges to act as locators to locate the device against an external surface.

9. The device as claimed in claim 1, wherein the length of the cannula is an adjustable length based on a distance from a skin tissue to the target site.

10. The device as claimed in claim 1, wherein a length, a cross-section, and a speed of motion of the plunger are controlled to control fluid delivery parameters of the one or more fluids, and wherein the fluid delivery parameters comprise volume and flow rate of the one or more fluids.

11. The device as claimed in claim 1, wherein the length of the cannula is a fixed length.

* * * * *